(12) United States Patent
Zhuang et al.

(10) Patent No.: US 12,128,161 B2
(45) Date of Patent: Oct. 29, 2024

(54) STERILIZATION DEVICE, AIR FILTER, AND FILTRATION SYSTEM

(71) Applicant: SHENZHEN YITOA INTELLIGENT INDUSTRIAL CO., LTD, Shenzhen (CN)

(72) Inventors: Junhuang Zhuang, Shenzhen (CN); Shujie Wang, Shenzhen (CN); Zhihong Zheng, Shenzhen (CN)

(73) Assignee: SHENZHEN YITOA INTELLIGENT INDUSTRIAL CO., LTD, Shenzhen (CN)

( * ) Notice: Subject to any disclaimer, the term of this patent is extended or adjusted under 35 U.S.C. 154(b) by 527 days.

(21) Appl. No.: 17/577,526

(22) Filed: Jan. 18, 2022

(65) Prior Publication Data

US 2023/0073579 A1    Mar. 9, 2023

(30) Foreign Application Priority Data

Sep. 7, 2021   (CN) .......................... 202111045451.3
Sep. 7, 2021   (CN) .......................... 202122153554.3

(51) Int. Cl.
*B01D 46/00*   (2022.01)
*A61L 9/20*    (2006.01)
*G02B 5/08*    (2006.01)

(52) U.S. Cl.
CPC ............ *A61L 9/20* (2013.01); *B01D 46/0028* (2013.01); *G02B 5/0891* (2013.01); *A61L 2209/14* (2013.01); *B01D 2279/65* (2013.01)

(58) Field of Classification Search
CPC .... A61L 9/20; A61L 2209/14; A61L 2209/12; B01D 46/0028; B01D 2279/65; B01D 46/10; G02B 5/0891; F24F 8/108; F24F 8/22
See application file for complete search history.

(56) References Cited

U.S. PATENT DOCUMENTS

| | | | |
|---|---|---|---|
| 9,851,066 B2* | 12/2017 | Kropac | F21S 43/14 |
| 10,371,338 B2* | 8/2019 | Haberkorn | G02B 27/30 |
| 2005/0238551 A1* | 10/2005 | Snyder | A61L 9/205 |
| | | | 422/186.3 |
| 2007/0291471 A1* | 12/2007 | Moon | G02F 1/133608 |
| | | | 362/97.1 |
| 2015/0338564 A1* | 11/2015 | Zhang | G02B 6/0036 |
| | | | 362/613 |
| 2022/0186953 A1* | 6/2022 | Kim | F24F 8/108 |
| 2022/0362419 A1* | 11/2022 | Tanaka | A61L 2/10 |

(Continued)

*Primary Examiner* — Dung H Bui
(74) *Attorney, Agent, or Firm* — Li & Cai Intellectual Property (USA) Office

(57) ABSTRACT

Provided are a sterilization device, an air filter, and a filtration system, which relate to the technical filed of sterilization equipment. The sterilization device includes an ultraviolet (UV) lamp module, two cover plates arranged opposite each other, and two reflecting layers, where a flow chamber which allows the air to flow therein is formed between the two cover plates, and each of the two cover plates is provided with at least one air vent communicated with the flow chamber; wherein two opposite surfaces of the two cover plates respectively have the two reflecting layers disposed thereon, and at least one of the two reflecting layers is a diffuse reflection layer; and the UV lamp module is disposed on the cover plate and is used to emit UV light into the flow chamber.

4 Claims, 6 Drawing Sheets

(56) References Cited

U.S. PATENT DOCUMENTS

| | | | |
|---|---|---|---|
| 2023/0146065 A1* | 5/2023 | Lan | A61L 9/20 422/24 |
| 2024/0077198 A1* | 3/2024 | Van Bommel | F21V 7/043 |
| 2024/0240817 A1* | 7/2024 | Toyoda | A61L 9/20 |

* cited by examiner

STERILIZATION DEVICE, AIR FILTER, AND FILTRATION SYSTEM

FIELD OF THE DISCLOSURE

The present disclosure relates to the technical field of sterilization equipment, and more particularly to a sterilization device, an air filter, and a filtration system.

BACKGROUND OF THE DISCLOSURE

At present, the conventional air filters use a filter element to filter the air. However, the filter element can only intercept the dust, but has a limited filtering effect for small bacteria and viruses. Further, the bacteria and viruses adhere to the filter element and multiply, leading to a great safety hazard. In order to kill the bacteria and viruses, UV lamps are disposed in the filter in the prior art to realize sterilization by means of direct irradiation with UV light. However, the utilization of the UV light is low, resulting in an undesired sterilization effect.

SUMMARY OF THE DISCLOSURE

The present application aims to provide a sterilization device, an air filter, and a filtration system, so as to overcome the inadequacies in the prior art.

To achieve the foregoing objectives, in a first aspect, the present application provides a sterilization device, which includes an ultraviolet (UV) lamp module, two cover plates arranged opposite each other, and two reflecting layers, where
  a flow chamber which allows the air to flow therein is formed between the two cover plates, and each of the two cover plates is provided with at least one air vent communicated with the flow chamber;
  wherein two opposite surfaces of the two cover plates respectively have the two reflecting layers disposed thereon, and at least one of the two reflecting layers is a diffuse reflection layer;
  wherein the UV lamp module is disposed on the cover plate and is used to emit UV light into the flow chamber.

With reference to the first aspect, in a possible implementation, an alternately concave and convex reflection surface is formed on the diffuse reflection layer.

With reference to the first aspect, in a possible implementation, the air vents on the two cover plates are staggered with each other.

With reference to the first aspect, in a possible implementation, multiple ones of the air vents are arranged on each of the two cover plates.

With reference to the first aspect, in a possible implementation, the multiple ones of air vents is evenly distributed on a side face of the cover plate that is away from the flow chamber.

With reference to the first aspect, in a possible implementation, the reflecting layer is disposed on the cover plate by means of coating or bonding.

With reference to the first aspect, in a possible implementation, the UV lamp module includes a predetermined number of UV LED light strips that are disposed on the cover plate.

With reference to the first aspect, in a possible implementation, a plurality of mounting grooves corresponding to the predetermined number of UV LED light strips are provided on the cover plate, and a light hole that allows the UV light to pass through is provided in each of the plurality of mounting grooves.

In a second aspect, the present application further provides an air filter, which includes a filter element assembly and the sterilization device provided in the first aspect, where the filter element assembly is disposed on a side of one of the two cover plates that is away from another one of the two cover plates.

In a third aspect, the present application further provides a filtration system, which includes the air filter provided in the second aspect.

Compared to the prior at, the present application has the following advantageous effects:

The sterilization device provided by the present application includes a UV lamp module, two cover plates arranged opposite each other, and two reflecting layers, where a flow chamber which allows the air to flow therein is formed between the two cover plates, and each of the two cover plate is provided with at least one air vent communicated with the flow chamber; wherein two opposite surfaces of the two cover plates respectively have the two reflecting layers disposed thereon, and at least one of the two reflecting layers is a diffuse reflection layer; wherein the UV lamp module is disposed on the cover plate and is used to emit UV light into the flow chamber. In the sterilization device provided by the present application, the air enters the flow chamber from the air vents on one of the cover plates, and the UV light emitted from the UV lamp module irradiates one of the reflecting layers. Because at least one of the two reflecting layers is a diffuse reflection layer and the diffuse reflection layer has a diffuse reflection surface, when the UV light irradiates or is reflected onto the diffuse reflection surface, the UV light is diffusely reflected on the diffuse reflection surface to present a "multidirectional" scattering effect, thus avoiding the energy from being overly concentrated in one direction. Therefore, the radiation light can be evenly distributed in the whole flow chamber by means of diffuse reflection, and the radiation energy can be retained in the flow chamber at the maximum extent, thus greatly improving the utilization of the UV light and achieving an efficient sterilization purpose.

In addition, because at least one of the two reflecting layers is a diffuse reflection layer, when the air flows in the flow chamber, a turbulent flow may be produced due to the irregularity of diffuse reflection of the diffuse reflection layer. Thus, the stay of the air in the flow chamber is prolonged, and the irradiation duration of the UV light to the air is increased, thus improving the sterilization effect.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

To describe the technical solutions in the embodiments of the present disclosure more clearly, the following briefly introduces the accompanying drawings required in the embodiments. It should be noted that, the accompanying drawings in the following description show merely some embodiments of the present disclosure and should not be regarded as limitations to the scope. Those of ordinary skill in the art can still derive other related drawings from these accompanying drawings without creative efforts.

MEANINGS OF NUMERAL

Figure 1:
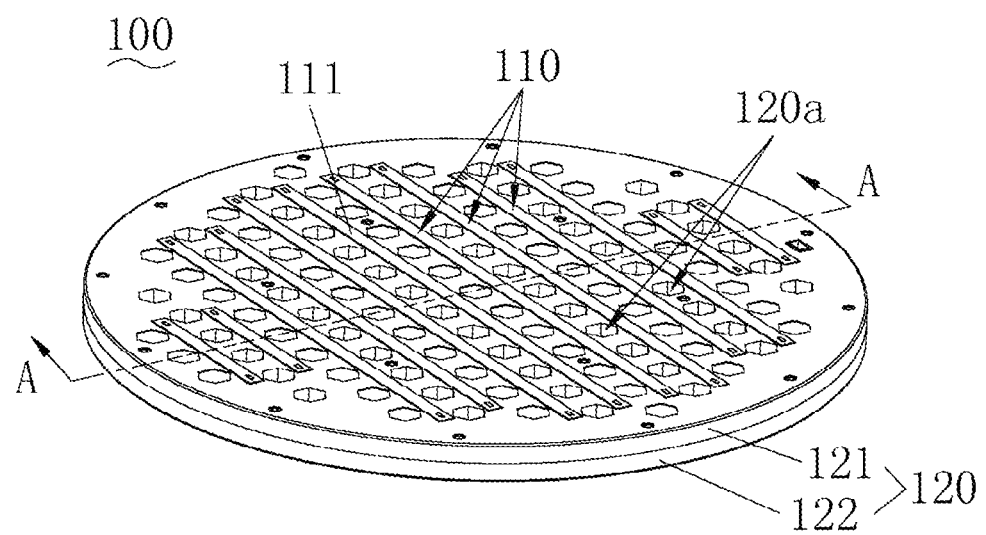
FIG. 1 is a schematic three-dimensional structural diagram of a sterilization device provided in an embodiment of the present application.

100. Sterilization device; 110. UV lamp module; 111. UV LED light strip; 120. Cover plate; 120a. Air vent; 120b. Flow chamber; 121. First cover plate; 1210. First air vent; 1211. First air guide sleeve; 1212. Mounting groove; 1213. Light hole; 121a. First side face; 121b. Second side face; 121c. First groove; 122. Second cover plate; 1220. Second air vent; 1221. Second air guide sleeve; 122a. Third side face; 122b. Fourth side face; 122c. Second groove; 130. Reflecting layer; 131. First reflecting layer; 131a. Through hole; 132. Second reflecting layer

DETAILED DESCRIPTION OF THE EXEMPLARY EMBODIMENTS

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

The embodiments of the present disclosure are described in detail below. Examples of these embodiments are shown in the accompanying drawings, in which the same or similar numerals indicate the same or similar elements or elements with the same or similar functions. The embodiments described below with reference to the accompanying drawings are exemplary and only used to explain the present disclosure, but cannot be understood as limitations to the present disclosure.

In the description of the present disclosure, it should be noted that, the orientations or positional relationships indicated by the terms "center", "longitudinal", "transverse", "length", "width", "thickness", "upper", "lower", "front", "rear", "left", "right", "vertical", "horizontal", "top", "bottom", "inner", "outer", "clockwise", "counterclockwise", "axial", "radial", "circumferential", etc. are based on the orientations or positional relationships shown in the accompanying drawings, and are only used for the convenience of describing the present disclosure and simplifying the description, rather than indicating or implying that the denoted device or element must have a specific orientation or be constructed and operated in a specific orientation. Therefore, these terms cannot be understood as limitations to the present disclosure.

In addition, the terms "first" and "second" are only used for descriptive purposes, and cannot be understood as indicating or implying relative importance or implicitly indicating the number of indicated technical features. Thus, the features defined with "first" and "second" may explicitly or implicitly include one or more of these features. In the description of this present disclosure, "multiple" means two or more than two, unless otherwise specifically defined.

In the present disclosure, unless expressly stipulated and limited otherwise, the terms "installation", "connected", "joined", "fixed" and other terms should be understood in a broad sense. For example, these terms may indicate a fixed connection or removable connection, or integration into a whole; or indicate mechanical connection or electrical connection; or mean direct connection or indirect connection via an intermediate medium, or internal communication or interaction between two components. For those of ordinary skill in the art, the specific meanings of the above terms in the present disclosure can be understood according to specific situations.

In the present disclosure, unless expressly stipulated and defined otherwise, the first feature "above" or "below" the second feature may be that the first and second features are in direct contact, or in indirect contact via an intermediate medium. Moreover, the first feature "above", "over" and "on" the second feature may mean that the first feature is directly above or obliquely above the second feature, or simply mean that the level of the first feature is higher than that of the second feature. The first feature "below", "under" and "beneath" the second feature may mean that the first feature is directly below or obliquely below the second feature, or simply mean that the level of the first feature is lower than the second feature.

First Embodiment

Figure 2:
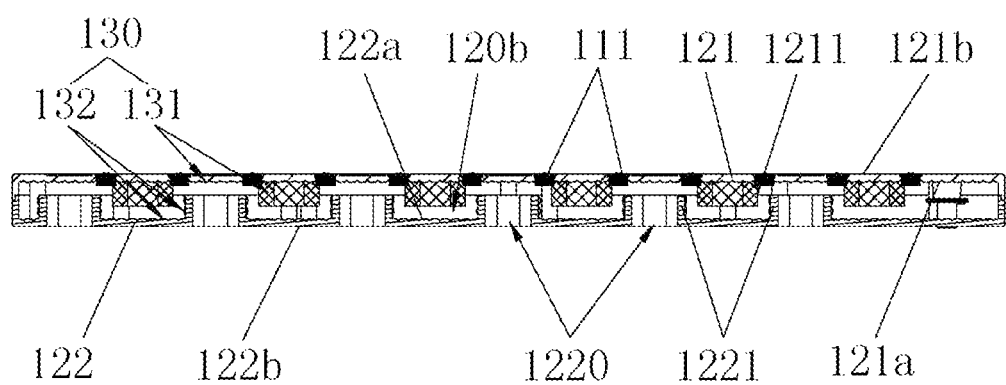
FIG. 2 is a sectional diagram of FIG. 1 in A-A direction.

Referring to FIGS. 1 and 2, this embodiment provides a sterilization device 100, which is used to sterilize the air passing through the sterilization device 100.

The sterilization device 100 provided by the present application includes a UV lamp module 110, two cover plates 120 arranged opposite each other, and two reflecting layers 130. A flow chamber 120b which allows the air to flow therein is formed between the two opposite cover plates 120, each of the two cover plates 120 is provided with at least one air vent 120a, and the at least one air vent 120a is communicated with the flow chamber 120b. Two opposite surfaces of the two cover plates 120 respectively have the two reflecting layers 130 disposed thereon. The UV lamp module 110 is disposed on one of the cover plates 120, and can emit UV light into the flow chamber 120b; and the UV light may be reflected when irradiating the reflecting layer 130.

Further, in order to describe the technical solution of this embodiment more clearly, the two cover plates 120 are defined as a first cover plate 121 and a second cover plate 122 respectively. Correspondingly, the air vent 120a provided on the first cover plate 121 is a first air vent 1210, and the air vent 120a provided on the second cover plate 122 is a second air vent 1220.

Alternatively, the first cover plate 121 and the second cover plate 122 match in shape; and may be cylindrical, prismatic, or in other shapes. The first air vent 1210 and the second air vent 1220 may be in other different shapes such as a circle, square, hexagon, and the like.

The first cover plate 121 has a first side face 121a and a second side face 121b that are opposite each other; and the second cover plate 122 has a third side face 122a and a fourth side face 122b that are opposite each other. The first side face 121a of the first cover plate 121 and the third side face 122a of the second cover plate 122 are close to each other; and the second side face 121b of the first cover plate 121 and fourth side face 122b of the second cover plate 122 are close to each other.

Further, the first cover plate 121 and the second cover plate 122 are clamped or connected with screws, for ease of assembly/disassembly and maintenance.

Figure 3:
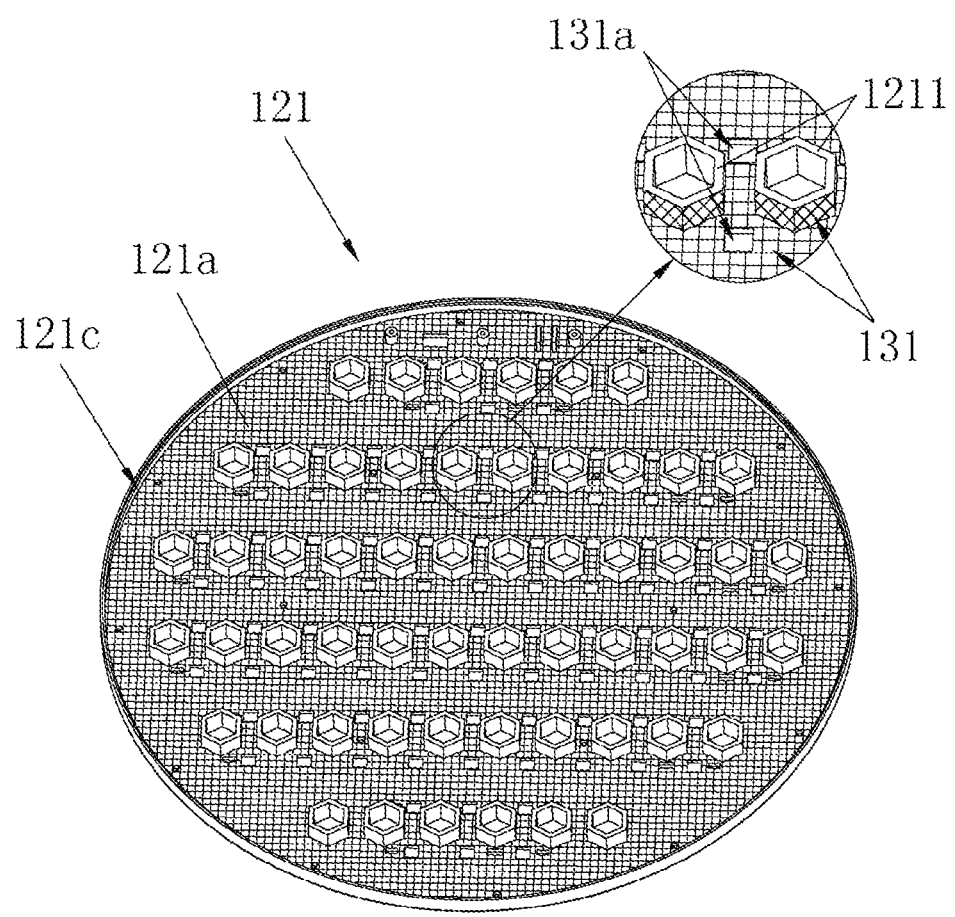
FIG. 3 is a schematic three-dimensional structural diagram of a back side of a first cover plate in the sterilization device shown in FIG. 1.
Figure 5:
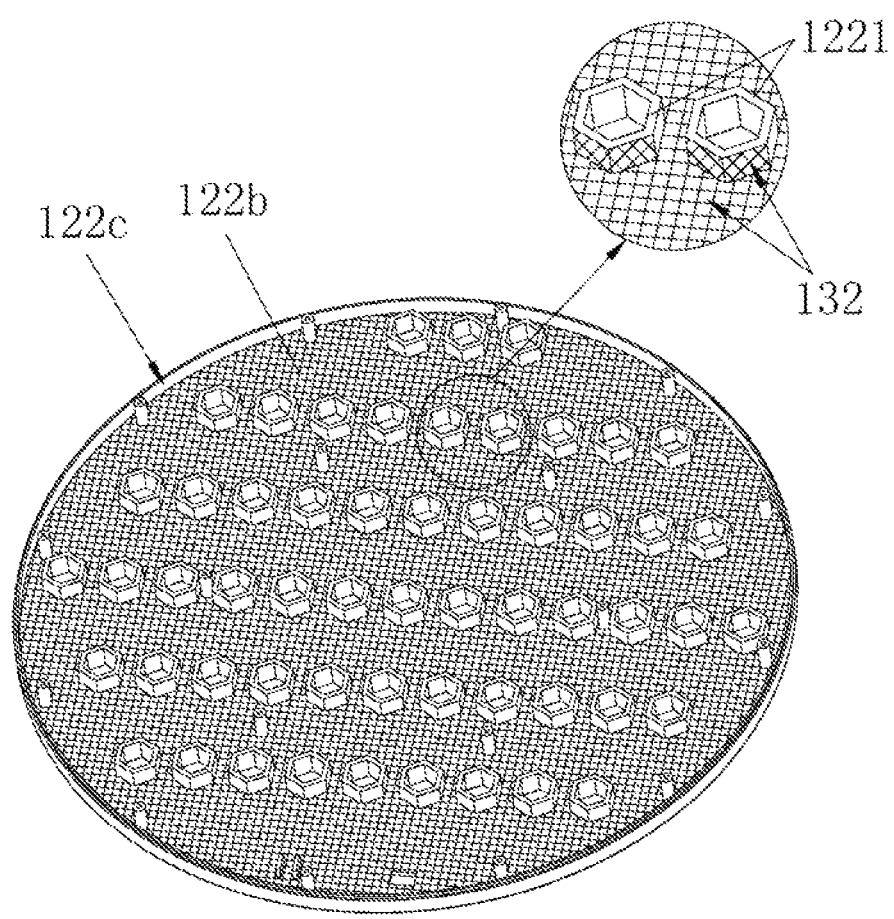
FIG. 5 is a schematic three-dimensional structural diagram of a back side of a second cover plate in the sterilization device shown in FIG. 1.

Referring to FIGS. 2, 3, and 5, a first groove 121c is recessed in the first side face 121a towards the interior of the first cover plate 121, and a second groove 122c is recessed in the third side face 122a towards the second cover plate 122. When the first side face 121a and the third side face 122a get close to each other, the first groove 121c and the second groove 122c cooperate to form the flow chamber 120b which allows the air to flow. The first air vent 1210 on the first cover plate 121 and the second air vent 1220 on the second cover plate 122 are both communicated with the flow chamber 120b, so that the air can enter the flow chamber 120b from the first air vent 1210 and then flows out from the second air vent 1220; or the air can enter the flow chamber 120b from the second air vent 1220 and then flows out from the first air vent 1210.

Figure 4:
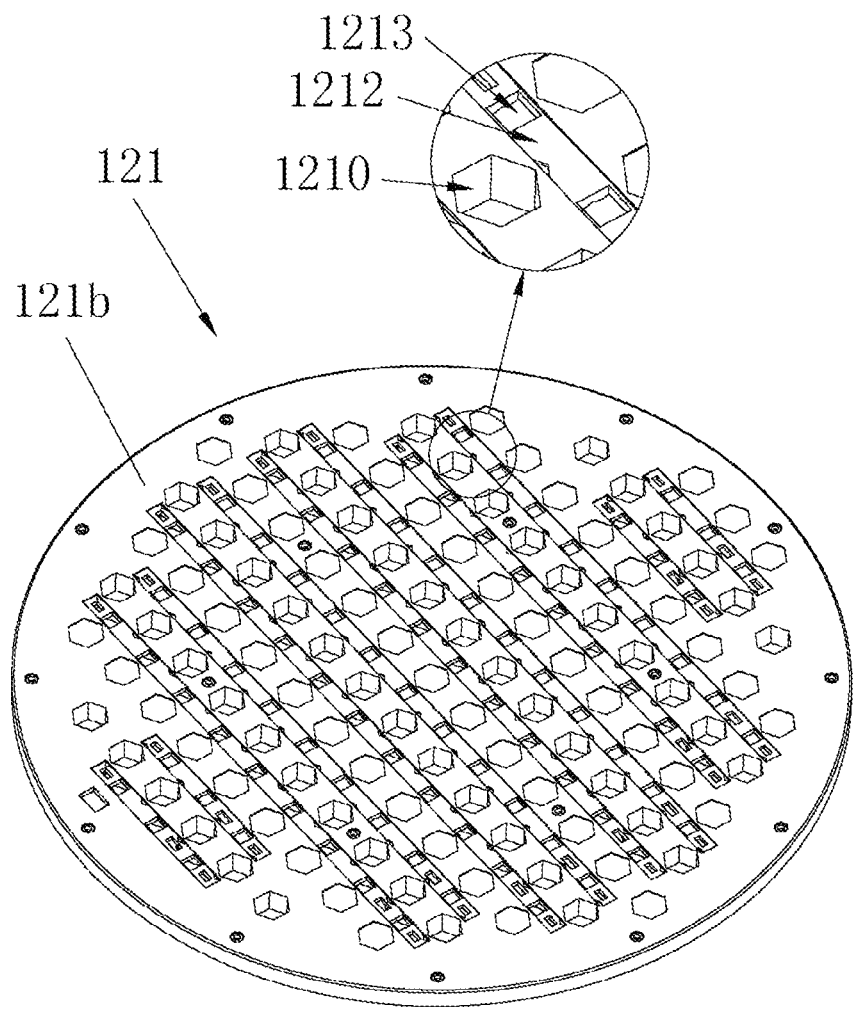
FIG. 4 is a schematic three-dimensional structural diagram of a front side of the first cover plate in the sterilization device shown in FIG. 1.
Figure 6:
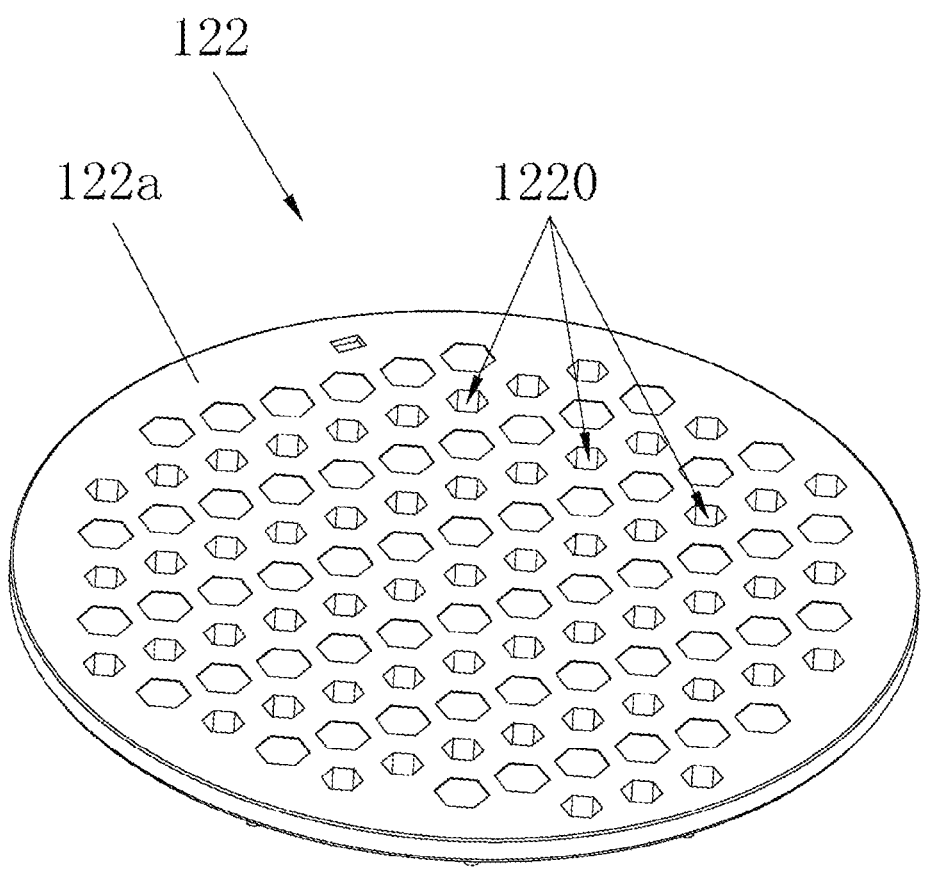
FIG. 6 is a schematic three-dimensional structural diagram of a front side of the second cover plate in the sterilization device shown in FIG. 1.

Then referring to FIGS. 4 and 6, further, there is a plurality of first air vents 1210 on the first cover plate 121, and the plurality of first air vents 1210 are evenly arranged on the second side face 121b of the first cover plate 121; and there is a plurality of second air vents 1220 on the second cover plate 122, and the plurality of second air vents 1220 are evenly arranged on the fourth side face 122b of the second cover plate 122, so that the air can smoothly enter the flow chamber 120b and then flow out of the flow chamber 120b.

Alternatively, the adjacent first air vent 1210 and second air vent 1220 are staggered with each other. Thus, the air is unlikely to directly pass through the first air vent 1210 and the second air vent 1220, and a flow path of the air into the flow chamber 120b is relatively far, thus prolonging the flow duration of the air in the flow chamber 120b.

Referring to FIGS. 2, 3, and 5, in this embodiment, the two reflecting layers 130 are defined as a first reflecting layer 131 and a second reflecting layer 132 respectively. The first reflecting layer 131 is disposed on the bottom of the first groove 121c on the first side face 121a, or on the bottom and sidewalls of the first groove 121c. The second reflecting layer 132 is disposed on the bottom of the second groove 122c on the third side face 122a, or on the bottom and sidewalls of the second groove 122c.

It should be understood that, because the first side face 121a of the first cover plate 121 and the third side face 122a of the second cover plate 122 are arranged opposite each other, the first reflecting layer 131 on the bottom of the first groove 121c and the second reflecting layer 132 on the bottom of the second groove 122c are also arranged opposite each other.

Alternatively, the first reflecting layer 131 and the second reflecting layer 132 are formed on the corresponding first cover plate 121 and second cover plate 122 by a process of coating; or the first reflecting layer 131 and the second reflecting layer 132 are both disposed on the corresponding first cover plate 121 and second cover plate 122 by a process of bonding.

Referring to FIGS. 1, 2, and 4, the UV lamp module 110 includes a predetermined number of UV LED light strips 111 that are disposed on the first cover plate 121 or the second cover plate 122. In this embodiment, the predetermined number of UV LED light strips 111 are disposed on the second side face 121b of the first cover plate 121. It can be understood that, the number of the UV LED light strips 111 is determined according to the area of the second side face 121b, and is not limited in this embodiment.

Specifically, each UV LED light strip 111 is disposed with a plurality of LED beads which can emit UV light. A plurality of mounting grooves 1212 corresponding to the predetermined number of UV LED light strips 111 are provided on the second side face 121b of the first cover plate 121, and the mounting grooves 1212 and the first air vents 1210 do not interfere with each other. Light holes 1213 corresponding to the LED beads are provided in each mounting groove 1212, and run through the second side face 121b to the first side face 121a. The first reflecting layer 131 is provided with through holes 131a corresponding to the light holes 1213. Thus, the UV light emitted from each LED bead passes through the corresponding light hole 1213 and through hole 131a successively, and then directly irradiates the second reflecting layer 132 on the second cover plate 122.

It can be understood that, this embodiment adopts LED beads that can emit UV light. The LED bead, as a continuous radiant energy generator, emits invisible light, but the emitted light is still in the form of light beams and thus also conforms to the principle of light reflection. Further because the first reflecting layer 131 and the second reflecting layer 132 are arranged opposite each other, the UV light is uninterruptedly reflected between the first reflecting layer 131 and the second reflecting layer 132, till the energy is depleted. Meanwhile, the LED beads still constantly emit energy, and the emitted light and the light that is still being reflected together preset a superposition effect, thus maximizing the radiation energy. Thus, the air flowing through the flow chamber 120b can be well sterilized to kill the bacteria and viruses in the air.

Further, because the adjacent first air vent 1210 and second air vent 1220 are staggered with each other, the flow duration of the air in the flow chamber 120b is prolonged, that is, the duration of radiation and sterilization of the UV light to the air is prolonged, thus improving the sterilization effect.

Definitely, in the foregoing situation, a very small amount of UV light may be reflected and enter the first air vents 1210 and the second air vents 1220 to interrupt the reflection, which does not affect the sterilization effect.

Referring to FIGS. 2, 3, and 5, in this embodiment, the first reflecting layer 131 and the second reflecting layer 132 are both diffuse reflection layers, and each diffuse reflection layer has a diffuse reflection surface. Thus, when the UV light irradiates or is reflected onto the diffuse reflection surface of the diffuse reflection layer, the UV light is diffusely reflected on the diffuse reflection surface to present a "multidirectional" scattering effect, thus avoiding the energy from being overly concentrated in one direction. Therefore, the radiation light can be evenly distributed in the whole flow chamber 120b by means of diffuse reflection, and the radiation energy can be retained in the flow chamber 120b at the maximum extent, thus greatly improving the utilization of the UV light and achieving an efficient sterilization purpose.

Further, an alternately concave and convex diffuse reflection surface is formed on the diffuse reflection layer, that is, the diffuse reflection surface is irregular and undulating. Therefore, the air flowing through the diffuse reflection surface also rises and falls accordingly, and then the air in the flow chamber is disturbed, so that the flowing air assumes a turbulent state. A relatively flat reflection surface can prolong the air flow path, thus prolonging the air retention time.

Therefore, the diffuse reflection design of the first reflecting layer 131 and the second reflecting layer 132 in this embodiment not only can achieve an optical effect, but also realize retention of the air flow, thus prolonging the duration of the air passing through the sterilization device 100, and further improving the sterilization effect of the module.

Definitely, in some embodiments, the first reflecting layer 131 or the second reflecting layer 132 is a diffuse reflection layer. For example, when the first reflecting layer 131 is a diffuse reflection layer and the second reflecting layer 132 is a specular reflection layer, a sterilization effect can also be achieved. It should be understood that, the foregoing description merely gives examples, and does not limit the protection scope of the present application.

Alternatively, the diffuse reflection surface of the diffuse reflection layer is a wavy arc surface, a concave and convex rhombic surface, honeycomb surface, or other incompletely planar surfaces. It should be noted that, the foregoing description merely gives examples, and does not limit the protection scope of the present application.

It should be further noted that, the air sterilizer using UV mercury lamps that is adopted in the prior art basically resorts to direct irradiation manner, which does not efficiently utilize the optical principle and also fails to maximize the energy utilization. Moreover, the mercury lamp has high energy, a tubular form, and inelastic optical design; and the gaseous mercury in the mercury lamp is a lethal, neurotoxic gas. Therefore, the use of solid-state LED beads to emit UV light in this embodiment achieves high safety. Further, considering that the current LED bead still has low UV radiation conversion efficiency, the optical design manner provided in this embodiment is used in combination, to improve its energy utilization, thus designing a relatively safe and effective sterilization product while realizing elasticity and flexibility of its structural design.

Moreover, because air is a fluid, when the air is taken as the object to be sterilized, its flow speed needs to be noted, which affects the success rate of air sterilization. Therefore, the sterilization device 100 provided in this embodiment can prolong the air retention time to a certain degree. Thus, under the condition of affecting the flow speed but not affecting the flow volume, in combination with efficient utilization of the UV light, the sterilization efficiency of the UV light can be maximized, and high safety can be achieved at the same time.

Second Embodiment

Referring to FIGS. 2 to 6, this embodiment provides a sterilization device 100, which makes improvements on the technical basis of the foregoing first embodiment; and has the following differences compared to the foregoing embodiment:

Referring to FIGS. 3 and 4, in this embodiment, a first air guide sleeve 1211 corresponding to each first air vent 1210 is disposed on the first cover plate 121; and is located at the bottom of the first groove 121c and extends away from the second side face 121b. An air channel is provided in the first air guide sleeve 1211 and is communicated with the corresponding first air vent 1210.

Referring to FIGS. 5 and 6, a second air guide sleeve 1221 corresponding to each second air vent 1220 is disposed on the second cover plate 122; and is located at the bottom of the second groove 122c and extends away from the fourth side face 122b. An air channel is provided in the second air guide sleeve 1221 and is communicated with the corresponding second air vent 1220.

Further referring to FIG. 2 in combination, when the first cover plate 121 and the second cover plate are arranged opposite each other, the opening of the first air guide sleeve 1211 faces the bottom of the second groove 122c, and the opening of the second air guide sleeve 1221 faces the bottom of the first groove 121c. For example, the air enters from the first air vents 1210, and is guided through the air channels of the first air guide sleeves 1211 to the bottom of the second groove 122c. The air with a certain flow speed strikes the bottom of the second groove 122c and then spreads in all directions, so that the air can be uniformly distributed in the flow chamber 120b, thus improving the sterilization effect. In addition, the air in the flow chamber 120b enters the air channels from the openings of the second air guide sleeves 1221 and then is discharged from the second air vents 1220, thus prolonging the air flow path, prolonging the sterilization duration, and improving the sterilization effect. Definitely, the same effect is achieved when the air enters from the second air vents 1220 and is discharged from the first air vents 1210, so the details are not described herein again.

Referring to FIGS. 3 and 5, further, a first reflecting layer 131 is correspondingly disposed on the outer side face of the first air guide sleeve 1211, and a second reflecting layer 132 is correspondingly disposed on the second air guide sleeve 1221. In this way, when reflected to the outer side faces of the first air guide sleeve 1211 and the second air guide sleeve 1221, the UV light can be further reflected, so that the UV light can be more evenly distributed in the flow chamber 120b, thus improving the utilization of the UV light and the sterilization effect.

Third Embodiment

Referring to FIGS. 1 to 6, this embodiment provides an air filter which is used to filter the dust in the air and further sterilize the air.

The air filter includes a filter element assembly and the sterilization device 100 provided in the foregoing first or second embodiment. The specific structure of the sterilization device 100 has been described in detail in the foregoing first or second embodiment, so the details are not described herein again. The filter element assembly is disposed on the second side face 121b of the first cover plate 121. Thus, the air first enters the flow chamber 120b from the second air vents 1220 of the second cover plate 122 for sterilization, and then flows out from the first air vents 1210 of the first cover plate 121 and enters the filter element assembly for filtering.

In some embodiments, the air is first filtered through the filter element assembly, then enters the flow chamber 120b from the first air vents 1210 of the first cover plate 121, and finally is discharged from the second air vents 1220 of the second cover plate 122.

This embodiment further provides a filtration system, which includes the foregoing air filter. Definitely, a plurality of air filters may be disposed in the filtration system.

In the description of the present specification, the reference terms "one embodiment", "some embodiments", "example", "specific example", "some examples" and the like mean that specific characteristics, structures, materials or features described with reference to the embodiments or examples are included in at least one embodiment or example of the present disclosure. In the present specification, the schematic description of the above terms does not have to be directed to the same embodiment or example. Furthermore, the described specific characteristics, structures, materials, or features may be combined in a suitable manner in any one or more of the embodiments or examples. In addition, those skilled in the art can integrate and combine different embodiments or examples and features of the different embodiments or examples described in the present disclosure, without contradicting each other.

Although the embodiments of the present application have been shown and described above, it can be understood that the foregoing embodiments are exemplary only and should not be construed as limiting the present disclosure. Those of ordinary skill in the art can make changes, modifications, substitutions, and modifications to the above-mentioned embodiments within the scope of the present disclosure.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An air filter, comprising:
   a filter element assembly; and
   the sterilization device;
   wherein the sterilization device comprises: an ultraviolet (UV) lamp module;
   two cover plates arranged opposite each other; and
   two reflecting layers;
   wherein a flow chamber which allows the air to flow therein is formed between the two cover plates, and each of the two cover plates is provided with at least one air vent communicated with the flow chamber;
   wherein two opposite surfaces of the two cover plates respectively have the two reflecting layers disposed thereon, and at least one of the two reflecting layers is a diffuse reflection layer;
   wherein the UV lamp module is disposed on the cover plate and is used to emit UV light into the flow chamber;
   wherein an alternately concave and convex reflection surface is formed on the diffuse reflection layer;
   wherein multiple ones of the air vents are arranged on each of the two cover plates;
   wherein the multiple ones of the air vents are evenly arranged on a side face of each of the two cover plates that is away from the flow chamber;
   wherein the UV lamp module includes a predetermined number of UV LED light strips that are disposed on the cover plate;
   wherein a plurality of mounting grooves corresponding to the predetermined number of UV LED light strips are provided on the cover plate, and a light hole that allows the UV light to pass through is provided in each of the plurality of mounting grooves;
   wherein the filter element assembly is disposed on a side of one of the two cover plates that is away from another one of the two cover plates.

2. A filtration system, comprising the air filter of claim 1.

3. The air filter according to claim 1, wherein the at least one air vent on one of the two cover plates and the at least one air vent on another one of the two cover plates are staggered with each other.

4. The air filter according to claim 1, wherein the reflecting layer is disposed on the cover plate by a process of coating or a process of bonding.

* * * * *